(12) United States Patent
Fujikake

(10) Patent No.: US 11,953,037 B2
(45) Date of Patent: Apr. 9, 2024

(54) PART FASTENING STRUCTURE AND MOUNTING TOOL

(71) Applicant: TOYOTA JIDOSHA KABUSHIKI KAISHA, Toyota (JP)

(72) Inventor: Yoshinori Fujikake, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 59 days.

(21) Appl. No.: 17/959,630

(22) Filed: Oct. 4, 2022

(65) Prior Publication Data
US 2023/0151840 A1 May 18, 2023

(30) Foreign Application Priority Data

Nov. 12, 2021 (JP) .................................. 2021-185075

(51) Int. Cl.
*F16B 21/00* (2006.01)
*A61F 5/01* (2006.01)
(Continued)

(52) U.S. Cl.
CPC ............ *F16B 19/00* (2013.01); *A61F 5/0123* (2013.01); *F16B 21/04* (2013.01); *Y10T 24/4578* (2015.01); *Y10T 403/7007* (2015.01)

(58) Field of Classification Search
CPC ........... Y10T 24/4578; Y10T 24/45812; Y10T 24/45801; Y10T 24/45796; Y10T 24/45785; Y10T 24/45749; Y10T 24/45743; Y10T 24/45728; Y10T 24/45717; Y10T 24/45712; Y10T 24/45702; Y10T 24/45696; Y10T 24/45686; Y10T 24/45681; Y10T 24/45675; Y10T 24/45602; Y10T 24/45262; Y10T 24/45251; Y10T 24/45241; Y10T 24/45225; Y10T 24/45;
(Continued)

(56) References Cited

U.S. PATENT DOCUMENTS 1,932,099 A * 10/1933 Cabana ................. A47L 13/252
403/349
3,478,302 A * 11/1969 Chirumbolo ......... H01R 13/623
403/349
(Continued)

FOREIGN PATENT DOCUMENTS

JP          2017-35220 A      2/2017

*Primary Examiner* — Robert Sandy
*Assistant Examiner* — Michael S Lee
(74) *Attorney, Agent, or Firm* — Oliff PLC

(57) ABSTRACT

A part fastening structure fastens a part, using a bolt and a nut. The bolt includes a first spiral groove, a second spiral groove provided on a tip end side of the bolt with respect to the first spiral groove, a slit extending from a tip end of the bolt to the first spiral groove through the second spiral groove, and a loosening suppression groove extending from another end of the second spiral groove to the tip end side. The nut includes: a first nut member including a first pin protruding toward a central axis side and inserted into the first spiral groove; a second nut member including a second pin protruding toward the central axis side and inserted into the second spiral groove; and an urging member disposed between the first and second nut members and that urges the first nut member toward a head portion of the bolt.

7 Claims, 10 Drawing Sheets

(51) Int. Cl.
*F16B 19/00* (2006.01)
*F16B 21/04* (2006.01)

(58) Field of Classification Search
CPC .... Y10T 24/42; Y10T 403/7007; F16B 21/04; F16B 19/00; A44B 99/005; A44C 5/2061; A44C 5/2057; A61F 5/0123
USPC .................................................. 24/DIG. 53
See application file for complete search history.

(56) References Cited

U.S. PATENT DOCUMENTS

| | | | | |
|---|---|---|---|---|
| 4,398,322 | A * | 8/1983 | Ewen | F16B 21/04 |
| | | | | D8/382 |
| 5,169,168 | A * | 12/1992 | Harry | B60D 1/07 |
| | | | | 403/349 |
| 2005/0276658 | A1 * | 12/2005 | Silva | F16G 15/06 |
| | | | | 403/154 |
| 2006/0099838 | A1 * | 5/2006 | Meyers | E02F 9/006 |
| | | | | 439/134 |
| 2007/0196196 | A1 * | 8/2007 | Schorling | F16B 21/04 |
| | | | | 411/555 |
| 2014/0105679 | A1 * | 4/2014 | Oliver | F16B 21/04 |
| | | | | 403/348 |
| 2015/0104247 | A1 * | 4/2015 | Wang | F16B 5/0208 |
| | | | | 403/349 |
| 2017/0035642 | A1 | 2/2017 | Sugata | |

* cited by examiner

PART FASTENING STRUCTURE AND MOUNTING TOOL

CROSS-REFERENCE TO RELATED APPLICATION

This application claims priority to Japanese Patent Application No. 2021-185075 filed on Nov. 12, 2021, incorporated herein by reference in its entirety.

BACKGROUND

1. Technical Field

The present disclosure relates to a part fastening structure and a mounting tool.

2. Description of Related Art

Japanese Unexamined Patent Application Publication No. 2017-35270 (JP 2017-35220 A) discloses a walking training device including a walking assisting device attached to a trainee's leg. The walking assist device includes a thigh frame and a lower leg frame. The thigh frame is attached to the trainee's thigh and the lower leg frame is attached to the trainee's lower leg.

SUMMARY

In such a walking training device, various trainees wear walking assist devices (also referred to as leg braces or mounting tools) for training. Thus, it is necessary for an assistant to adjust the walking assist device according to the trainee. For example, the assistant adjusts a frame length according to a length of a trainee's leg. In such a case, a part fastening structure for fastening two parts (for example, an upper frame and a lower frame) is used. That is, a frame is formed by fastening the two parts with the part fastening structure.

The frame length can be adjusted by the assistant loosening bolts and nuts and removing the two parts. That is, the assistant adjusts the frame length according to the leg length by changing the fastening position of the parts. Thus, it is desirable to easily and reliably attach and remove the parts. For example, it is desirable to attach and detach without a special tool. Further, a structure that does not loosen during use is desired.

The present disclosure has been made to solve such a problem, and provides a part fastening structure capable of simply and reliably fastening parts.

The part fastening structure in the present embodiment is a part fastening structure that fastens a part using a bolt and a nut. The bolt includes: a first spiral groove provided on a peripheral surface of the bolt; a second spiral groove that is provided on the peripheral surface of the bolt and that is provided on a tip end side of the bolt with respect to the first spiral groove; a slit that is provided on the peripheral surface of the bolt along an axial direction, and that extends from a tip end of the bolt to the first spiral groove through the second spiral groove; and a loosening suppression groove that extends from another end of the second spiral groove to the tip end side, the nut includes: a first nut member including a first pin that protrudes from an inner peripheral surface toward a central axis side and that is inserted into the first spiral groove; and a second nut member including a second pin that protrudes from the inner peripheral surface toward the central axis side and that is inserted into the second spiral groove; and an urging member that is disposed between the first nut member and the second nut member and that urges the first nut member toward a head portion of the bolt.

In the part fastening structure described above, the first spiral groove may be provided to be thicker than the second spiral groove, the first pin may be thicker than the second pin, and the first pin may be thicker than the second spiral groove.

In the part fastening structure described above, the first nut member may include: a cylindrical portion; and a dish portion protruding from the cylindrical portion to an outer peripheral side, the second nut member may be disposed on the outer peripheral side of the cylindrical portion, the cylindrical portion may be provided with a through hole extending through the cylindrical portion in a direction orthogonal to the axial direction, the through hole may be an elongated hole in which a longitudinal direction coincides with the axial direction, and the second pin may extend through the through hole.

In the part fastening structure described above, the urging member may be disposed between the dish portion and the second nut member.

In the part fastening structure described above, the first nut member may be provided with a plurality of the first pins spaced away from each other in a circumferential direction, the second nut member may be provided with a plurality of the second pins spaced away from each other in the circumferential direction, a plurality of the first spiral grooves may be provided corresponding to the first pins, a plurality of the second spiral grooves may be provided corresponding to the second pins, and a circumferential angle of the first spiral grooves and the second spiral grooves may be less than 180'.

In the part fastening structure described above, the nut may be provided with two first pins and two second pins, the two second pins may be disposed so as to face each other with a central axis in between, and the two first pins may be disposed so as to face each other with the central axis in between.

A mounting tool according to the present embodiment is a leg brace that is worn by a user, the mounting tool including: a first part including a plurality of first through holes; a second part including a second through hole; and the part fastening structure described above, in which the bolt is inserted through the first through hole and the second through hole.

According to the present disclosure, it is possible to provide a part fastening structure and a mounting tool capable of simply and reliably fastening parts.

BRIEF DESCRIPTION OF THE DRAWINGS

Features, advantages, and technical and industrial significance of exemplary embodiments of the disclosure will be described below with reference to the accompanying drawings, in which like signs denote like elements, and wherein.

DETAILED DESCRIPTION OF EMBODIMENTS

Hereinafter, the present disclosure will be described through embodiments of the disclosure. However, the disclosure according to the claims is not limited to the following embodiments. Moreover, all of the configurations described in the embodiments are not necessarily indispensable as means for solving the issue.

A part fastening structure 1 for fastening a first part 10 and a second part will be described with reference to FIGS. 1 to 4. The first part 10 and the second part 20 configure, for example, a frame to be attached to a leg of a trainee who performs walking training. Here, the first part 10 and the second part 20 are fastened by the part fastening structure 1 to form a frame disposed along a lower leg of the trainee. An assistant (also called a user) who assists the trainee adjusts the length of the frame according to the trainee.

Figure 1:
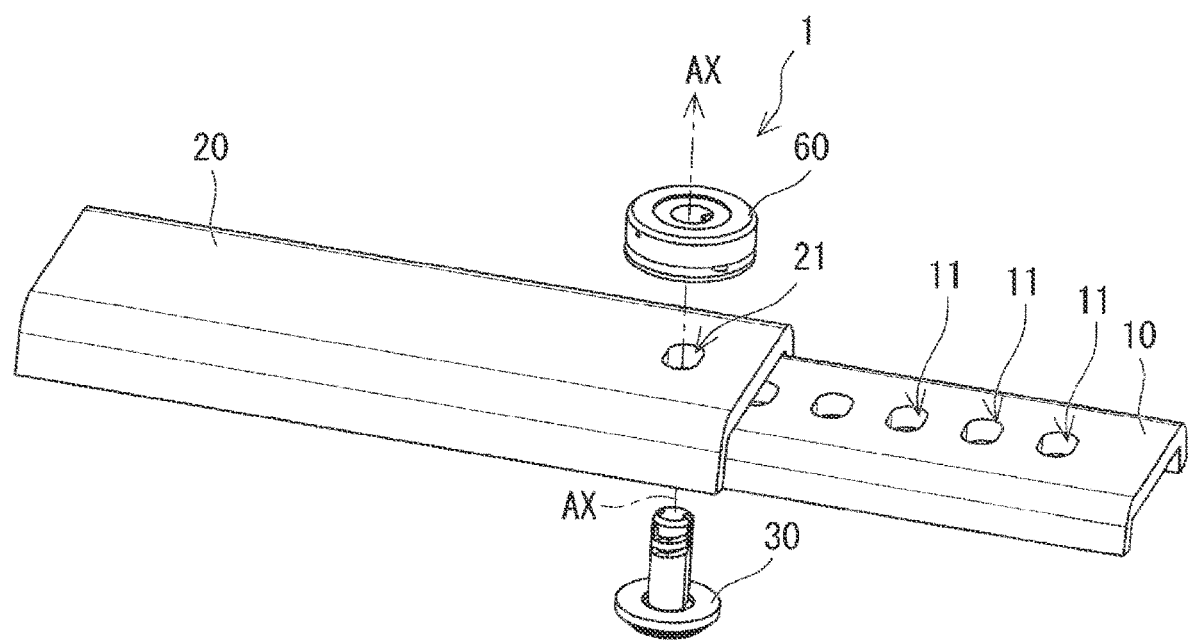
FIG. 1 is a perspective view showing the two parts fastened by the part fastening structure.
Figure 2:
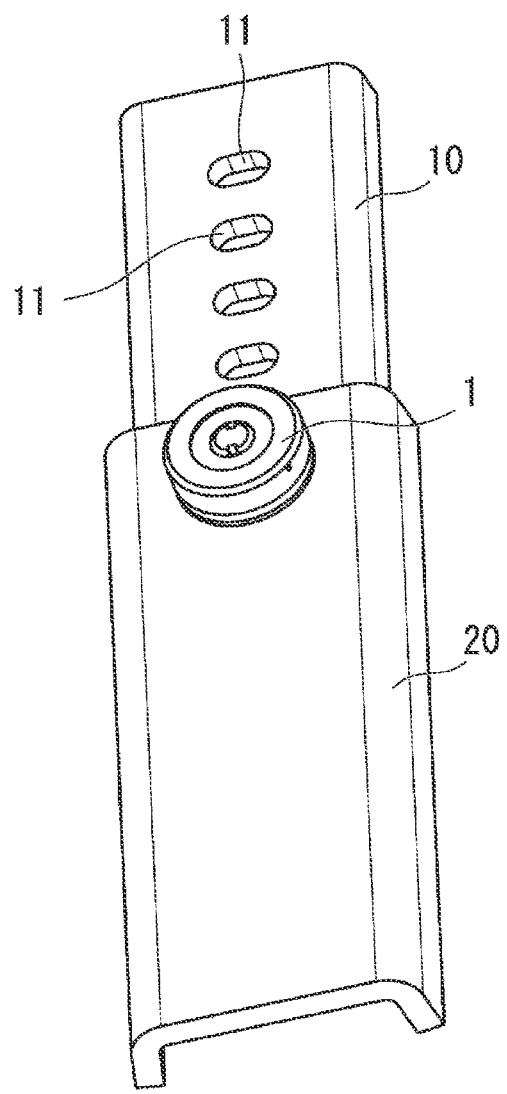
FIG. 2 is a perspective view showing the two parts fastened by the part fastening structure.
Figure 3:
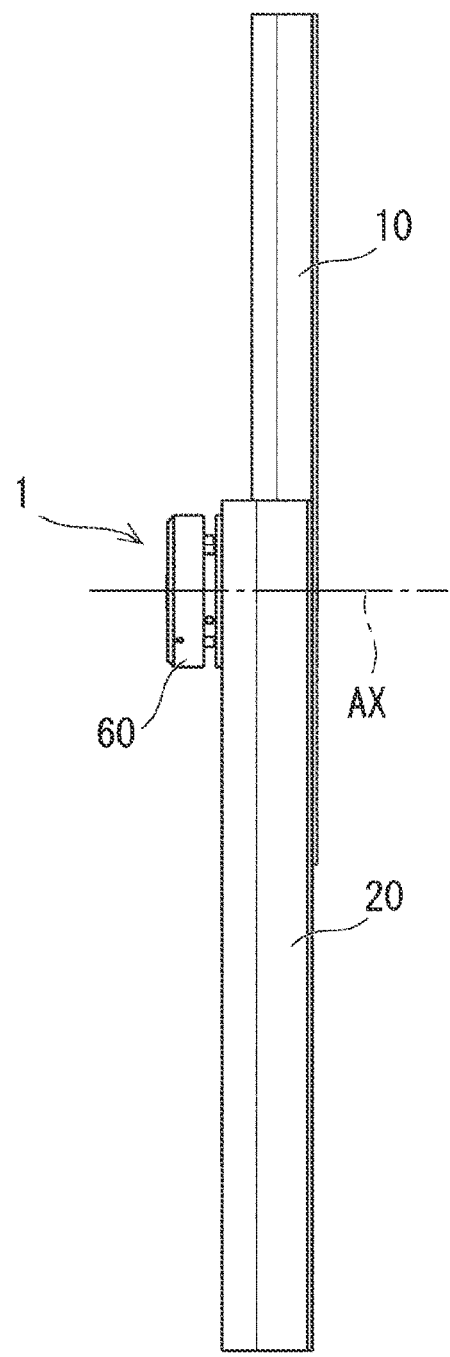
FIG. 3 is a side view of a fastening portion of the part fastening structure.
Figure 4:
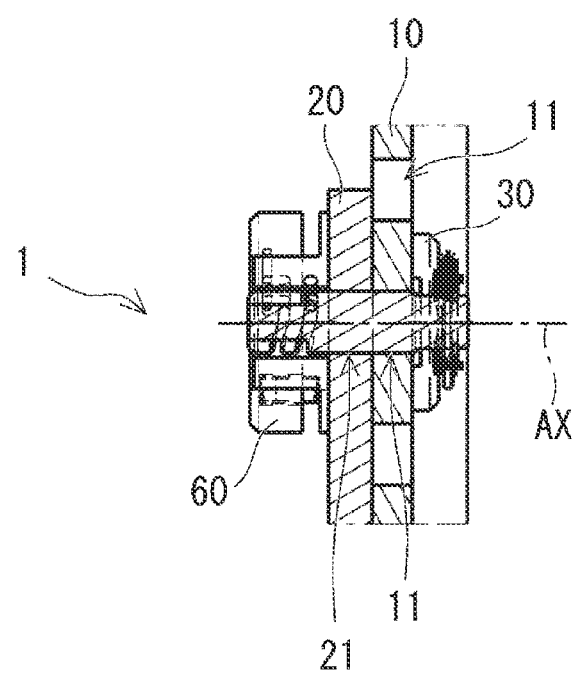
FIG. 4 is a perspective view of the fastening portion of the part fastening structure.

FIG. 1 is a perspective view showing a state before fastening. FIG. 2 is a perspective view showing a state after fastening. FIG. 3 is a side view showing a state after fastening. FIG. 4 is a diagram showing the part fastening structure that is cut.

One of the first part 10 and the second part 20 is disposed on an upper side, and the other is disposed on a lower side. Here, the first part 10 is disposed on a knee side and the second part 20 is disposed on an ankle side. The part fastening structure 1 is disposed laterally to a shin. Of course, the first part 10 and the second part 20 are not limited to the lower leg frame and the leg brace. Further, the vertical arrangement of the first part 10 and the second part 20 is not particularly limited.

The part fastening structure 1 includes a bolt 30 and a nut 60. In the part fastening structure 1, the first part 10 and the second part 20 are fastened using the bolt 30 and the nut 60. The bolt 30 is passed through holes provided in the first part 10 and the second part 20. In FIG. 1 and the like, a straight line along an axis center of the bolt 30 is shown as a central axis AX. The bolt 30 and the nut 60 are attached by rotating the bolt or the nut 60 around the central axis AX. By attaching the nut 60 to the bolt 30, the first part 10 and the second part 20 are fastened.

The first part 10 and the second part 20 are members whose longitudinal direction is along the lower leg. In FIG. 1, the first part 10 and the second part 20 are both channel steels. For example, the first part 10 and the second part 20 are each made of a metal material such as aluminum. A direction along the central axis AX is a thickness direction of the first part 10 and the second part 20.

As shown in FIGS. 1 and 2, the first part 10 is provided with a plurality of through holes 11. The through hole 11 extends through in the thickness direction of the first part 10. The through holes 11 are disposed in one row along the longitudinal direction of the first part 10. Here, the through holes 11 are formed at equal intervals along the longitudinal direction of the first part 10. Each of the through holes 11 has an elongated hole shape to suppress rotation on the bolt side. The through holes 11 have the same size and the same shape.

The second part 20 includes one through hole 21. The through hole 21 extends through the second part 20 in a thickness direction of the second part 20. The first part 10 and the second part 20 are disposed so as to partially overlap each other. The first part 10 and the second part 20 are disposed so that the through hole 21 of the second part 20 overlaps with one through hole 11 of the first part 10. The bolt 30 is inserted into the through hole 21 of the second part 20 and the through hole 11 of the first part 10. Then, the nut 60 is attached to the bolt 30 inserted into the through hole 11 and the through hole 21. As a result, the first part 10 and the second part 20 are fixed. Here, the bolt 30 is in contact with the first part 10 and the nut 60 is in contact with the second part 20.

Further, by changing the through hole 11 into which the bolt 30 is inserted, a length of an overlapping portion of the first part 10 and the second part 20 is changed. Thus, the total length of the frame can be adjusted. For example, by inserting the bolt 30 into the through hole 11 on the left side of FIG. 1 among the through holes 11, the overlapping portion of the first part 10 and the second part 20 is shortened. Thus, the frame length can be increased. By inserting the bolt 30 into the through hole 11 on the right side of FIG. 1 among the through holes 11, the overlapping portion of the first part 10 and the second part 20 becomes longer. Thus, the frame length can be shortened. In this way, the frame length can be made variable by changing the fastening position by the part fastening structure 1.

Figure 5:
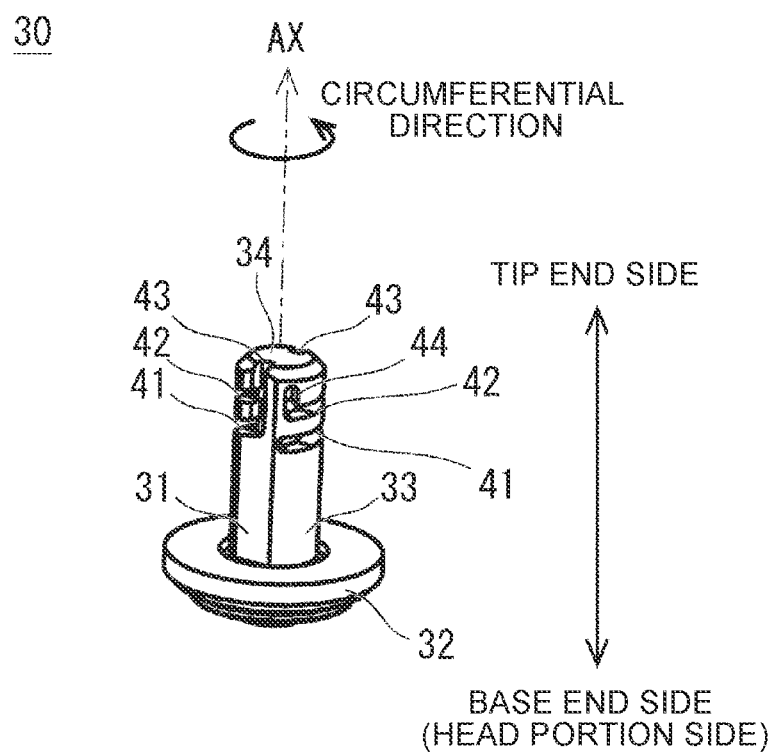
FIG. 5 is a perspective view showing the configuration of a bolt.
Figure 6:
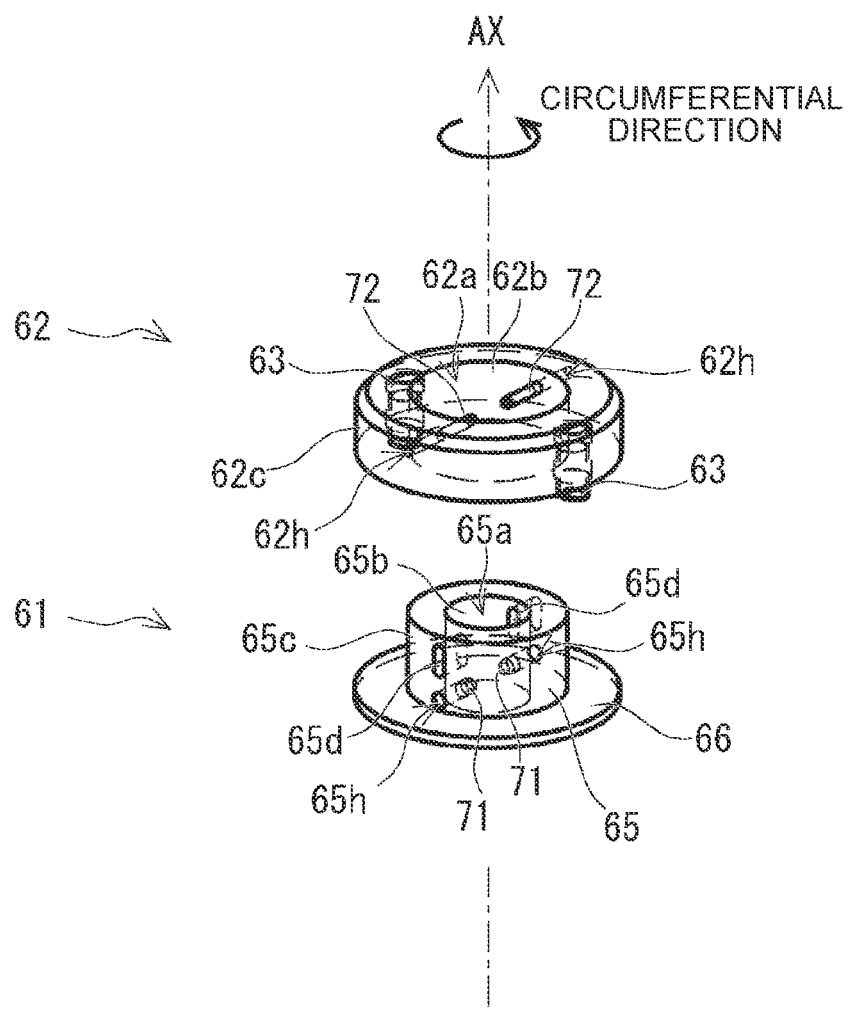
FIG. 6 is an exploded perspective view of a nut.
Figure 7:
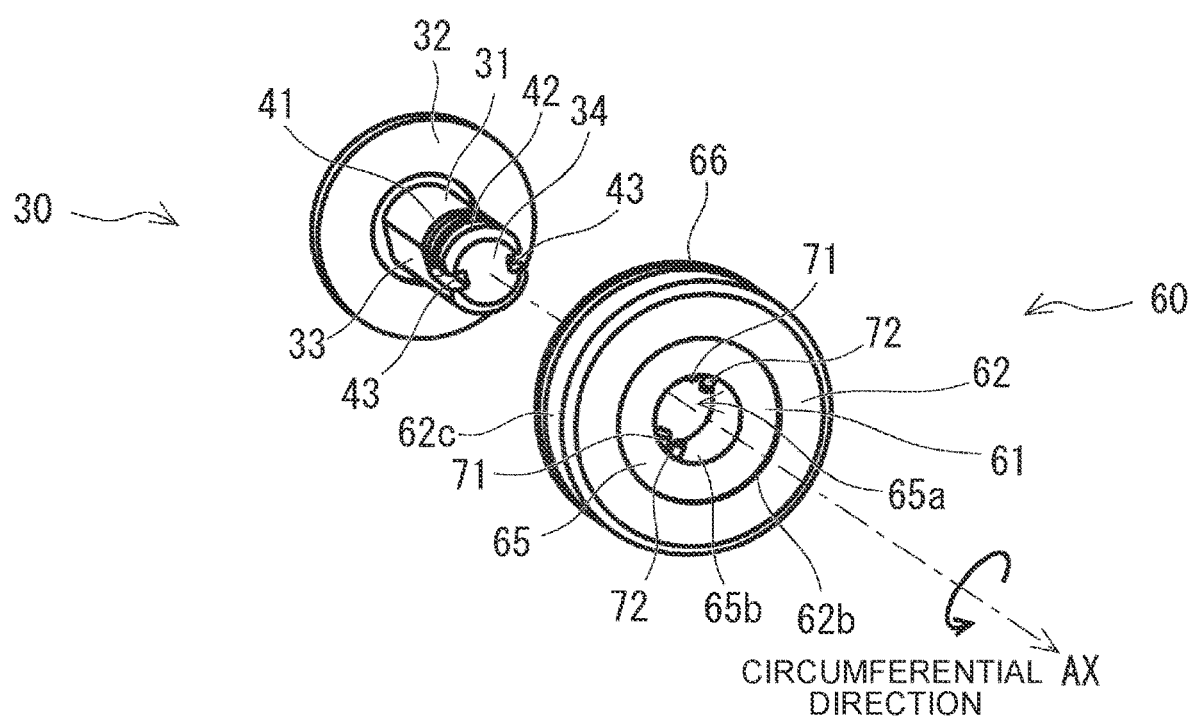
FIG. 7 is a perspective view showing a state before the bolt and the nut are attached.
Figure 8:
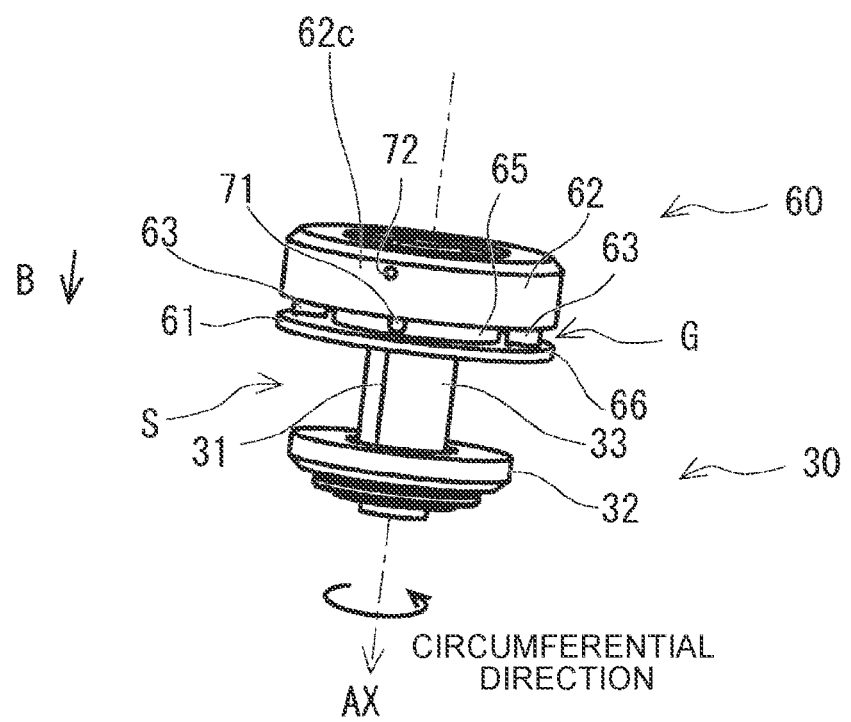
FIG. 8 is a perspective view showing a state in which the bolt and the nut are attached.
Figure 9:
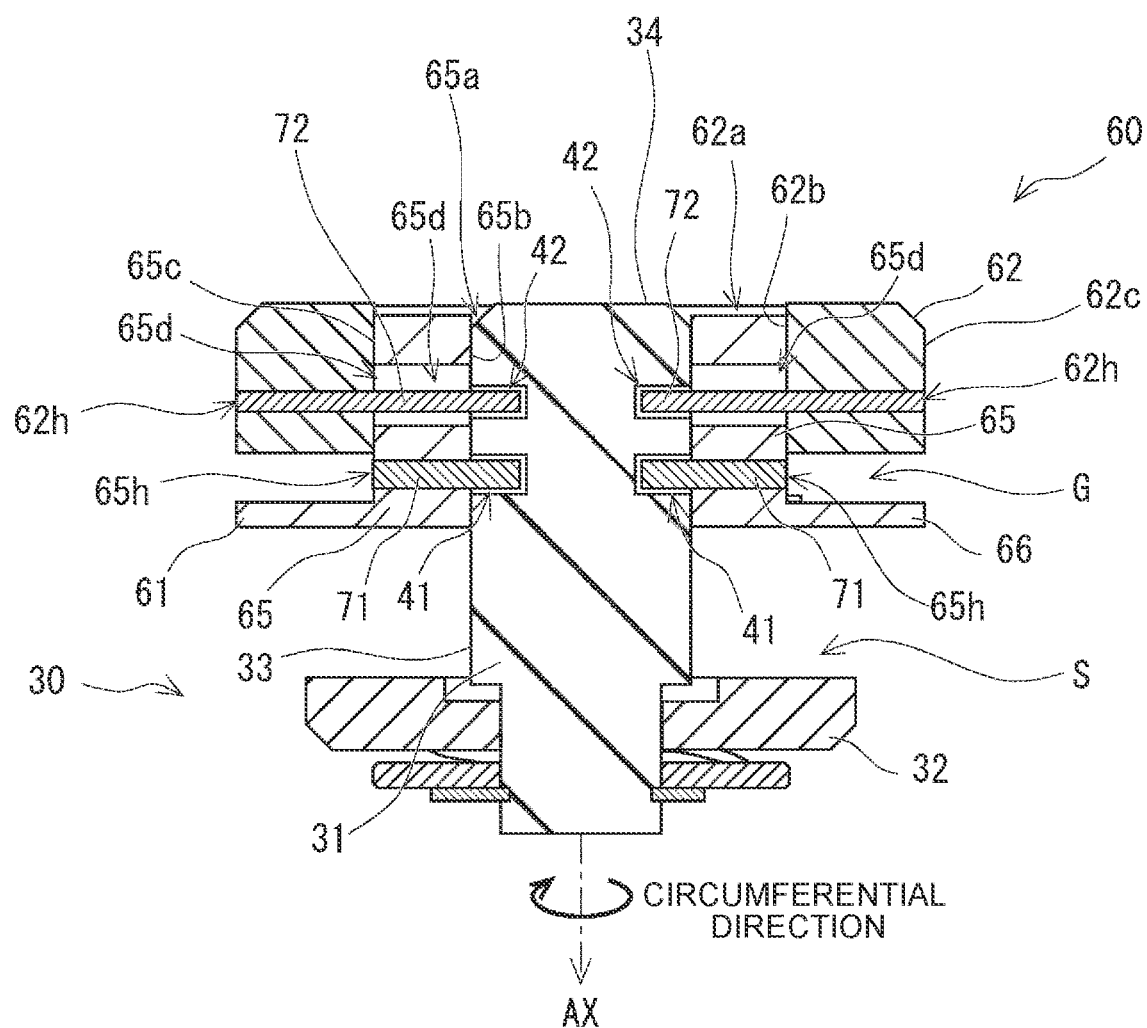
FIG. 9 is a cross-sectional view showing the part fastening structure that is cut.

Next, the part fastening structure 1 will be described with reference to FIGS. 5 to 9. FIG. 5 is a perspective view showing the configuration of the bolt 30. FIG. 6 is an exploded perspective view of the nut 60. FIG. 7 is a perspective view showing the part fastening structure 1 in a state before the bolt 30 and the nut 60 are attached. FIG. 8 is a perspective view showing the part fastening structure 1 in a state in which the bolt 30 and the nut 60 are attached. FIG. 9 is a cross-sectional view showing the part fastening structure 1 in a state in which the bolt 30 and the nut 60 are attached.

First, the configuration of the bolt 30 will be described with reference to FIG. 5 and the like. The bolt 30 includes a shaft portion 31 and a head portion 32. The shaft portion 31 is a substantially columnar portion, and is a portion inserted into the through hole 11 shown in FIG. 1 or the like. In FIG. 5, the center of the shaft portion 31 is defined as the central axis AX. A direction parallel to the central axis AX of the shaft portion 31 is defined as an axial direction. The axial direction is the direction in which the bolt 30 is inserted into the through hole 11. Further, as shown in FIG. 5, and the like, a direction around the central axis AX is defined as a circumferential direction. Thus, like a cylindrical coordinate system, a position in the circumferential direction is represented by an angle of 0 to 360° with a reference position (origin position) as 0°. As shown in FIG. 5, the head portion 32 side in the axial direction is a base end side, and the opposite side is a tip end side.

The shaft portion 31 includes a tip end surface 34 and a peripheral surface 33. The tip end surface 34 corresponds to a bottom surface of a cylinder, and the peripheral surface 33 corresponds to a side surface of the cylinder. The tip end surface 34 is provided on the tip end side of the shaft portion 31. The tip end surface 34 is the bottom surface located on the tip end side of the columnar shaft portion 31. The tip end surface 34 is a plane orthogonal to the central axis AX.

The head portion 32 is provided on the base end side of the shaft portion 31. The head portion 32 is a disc-shaped dish portion. An outer diameter of the head portion 32 is larger than an outer diameter of the shaft portion 31. The outer diameter of the shaft portion 31 is smaller than the through holes 11 and 21 so as to be inserted into the through holes 11 and 21. The outer diameter of the head portion 32 is larger than that of the through holes 11 and 21. Therefore, the head portion 32 comes into contact with the first part 10. A washer, a disc spring, or the like may be disposed between the head portion 32 and the first part 10.

The peripheral surface 33 is a portion from the tip end surface 34 to the head portion 32. That is, the peripheral surface 33 is a side surface (outer peripheral surface) of the shaft portion 31 having a substantially columnar shape. A first spiral groove 41, a second spiral groove 42, a slit 43, and a loosening suppression groove 44 are formed on the peripheral surface 33. The second spiral groove 42 is provided on the tip end side of the first spiral groove 41. In the axial direction, the second spiral groove 42 is disposed between the tip end surface 34 and the first spiral groove 41. That is, the first spiral groove 41 is disposed on the head portion 32 side, and the second spiral groove 42 is disposed on the tip end surface 34 side.

The first spiral groove 41 and the second spiral groove 42 are grooves (recess portions) formed in a spiral shape on the peripheral surface 33. The distance of the first spiral groove 41 from the tip end surface 34 changes in depending on the position (angle) in the circumferential direction. One end of the first spiral groove 41 is disposed on the tip end surface 34 side, and the other end is disposed on the head portion 32 side. Similarly, the distance of the second spiral groove 42 from the tip end surface 34 changes depending on the position in the circumferential direction. One end of the second spiral groove 42 is disposed on the tip end surface side, and the other end is disposed on the head portion 32 side. The first spiral groove 41 and the second spiral groove 42 are formed in parallel with each other. That is, the distance between the first spiral groove 41 and the second spiral groove 42 in the axial direction is constant. For example, when rotated by 90° in the circumferential direction, the position of the first spiral groove 41 shifts by 1 mm in the axial direction.

Further, the peripheral surface 33 of the bolt 30 is provided with the slit 43 formed along the axial direction. The slit 43 is a groove parallel to the central axis AX direction. The slit 43 extends from the tip end surface 34 to the first spiral groove 41. The slit 43 is connected to one end of the first spiral groove 41 on the tip end surface 34 side. The slit 43 is connected to one end of the second spiral groove 42 on the tip end surface 34 side. That is, the slit 43 reaches one end of the first spiral groove 41 from the tip end surface 34 via one end of the second spiral groove 42.

The loosening suppression groove 44 is connected to the second spiral groove 42. The loosening suppression groove 44 is a groove formed on the peripheral surface 33 along the axial direction. The loosening suppression groove 44 is formed from the other end of the second spiral groove 42 on the head portion 32 side toward the tip end surface 34 side. The loosening suppression groove 44 does not reach the tip end surface 34. That is, the length of the loosening suppression groove 44 in the axial direction is shorter than the distance from the tip end surface 34 to the other end of the second spiral groove 42. The slit 43 is connected to one end of the second spiral groove 42, and the loosening suppression groove 44 is formed at the other end.

Further, in the present embodiment, two slits 43 are formed on the peripheral surface 33. The two slits 43 are disposed so as to face each other with the central axis AX interposed therebetween. Similarly, the two loosening suppression grooves 44 are formed on the peripheral surface 33. The two loosening suppression grooves 44 are disposed so as to face each other with the central axis AX interposed therebetween.

Assuming that the position of one slit 43 in the circumferential direction is 0°, the position of the other slit 43 in the circumferential direction is 180°. That is, the two slits 43 are disposed symmetrically with respect to the central axis AX. Assuming that the position of one loosening suppression groove 44 in the circumferential direction is $\theta 1$, the position of the other loosening suppression groove 44 in the circumferential direction is ($\theta 1+180°$). Note that $\theta 1$ is less than 180°. That is, the two loosening suppression grooves 44 are disposed symmetrically with respect to the central axis AX.

Similarly, the two first spiral grooves 41 and the two second spiral grooves 42 are formed on the peripheral surface 33. In the circumferential direction, one first spiral groove 41 is formed so as not to overlap with the other first spiral groove 41. That is, the size (angle range) of each first spiral groove 41 in the circumferential direction is formed so as to be less than 180°.

Specifically, in the circumferential direction, one first spiral groove 41 is formed in the range of 0° to $\theta 1$, and the other first spiral groove 41 is formed in the range of 180° and above ($\theta 1+180°$), The two first spiral grooves 41 are disposed symmetrically with respect to the central axis AX. The circumferential angle of each first spiral groove 41 is less than 180°.

Similarly, in the circumferential direction, one second spiral groove 42 is formed so as not to overlap with the other second spiral groove 42. That is, the size (angle range) of each second spiral groove 42 in the circumferential direction is formed so as to be less than 180°.

Specifically, in the circumferential direction, one second spiral groove 42 is formed in the range of 0° to $\theta 1$, and the other second spiral groove 42 is formed in the range of 180° and above ($\theta 1+180°$). The two second spiral grooves 42 are disposed symmetrically with respect to the central axis AX. The circumferential angle of each second spiral groove 42 is less than 180°. Here, the first spiral groove 41 and the second spiral groove 42 have substantially the same length in the circumferential direction.

As described above, the circumferential angle of the first spiral groove 41 and the second spiral groove 42 is less than 180°. Thus, two first spiral grooves 41 and two second spiral grooves 42 can be formed on the peripheral surface 33. The peripheral surface 33 may be flat at the position in the circumferential direction in which the slit 43 is formed. The bolt 30 is made of a metal material such as iron or stainless steel. The diameter of the shaft portion 31 is about 7 mm to 8 mm.

Next, the configuration of the nut 60 will be described with reference to FIGS. 6, 7, and the like. The nut 60 includes a first nut member 61, a second nut member 62, and a spring 63. The second nut member 62 is a cylindrical member or a ring-shaped member. That is, the second nut member 62 is a member having a hollow portion 62a provided along the central axis AX. The hollow portion 62a is a columnar space along the axial direction. The surface of the second nut member 62 on the hollow portion 62a side is defined as an inner peripheral surface 62b. The outer peripheral surface of the second nut member 62 is referred to as an outer peripheral surface 62c.

The second nut member 62 has a second pin 72. For example, the second nut member 62 is formed with a pin hole 62h for fixing the second pin 72. The pin hole 62h is a through hole that reaches the inner peripheral surface 62b from the outer peripheral surface 62c.

The second pin 72 is press-fitted into the pin hole 62h from the outer peripheral surface 62c side. The second pin 72 protrudes from the inner peripheral surface 62b of the second nut member 62 toward the central axis AX side. The second pin 72 is disposed along a direction that passes through the central axis AX and that is extended along a direction orthogonal to the central axis AX. When the second pin 72 is inserted into the pin hole 62h, the second nut member 62 holds the second pin 72.

As shown in FIG. 9, the second pin 72 is inserted into the second spiral groove 42 of the bolt 30. Here, the second nut member 62 is provided with two second pins 72 and two pin holes 62h. A plurality of the second pins 72 is provided away from each other in the circumferential direction. The two second pins 72 are disposed symmetrically with respect to the central axis AX. That is, the two second pins 72 are disposed on the same straight line orthogonal to the central axis AX. The two second pins 72 correspond to the two second spiral grooves 42. That is, at the time of fastening the parts, one second pin 72 is inserted into one second spiral groove 42, and the other second pin 72 is inserted into the other second spiral groove 42.

As shown in FIG. 6 and the like, the first nut member 61 includes a cylindrical portion 65 and a dish portion 66. The cylindrical portion 65 is a cylindrical member having a hollow portion 65a. The hollow portion 65a is a columnar space along the axial direction. An outer diameter of the cylindrical portion 65 is smaller than a diameter of the hollow portion 62a of the second nut member 62. The cylindrical portion 65 is inserted, into the hollow portion 62a of the second nut member 62. The surface of the cylindrical portion 65 on the hollow portion 65a side is defined as an inner peripheral surface 65b. An outer peripheral surface of the cylindrical portion 65 is defined as the outer peripheral surface 65c. The outer peripheral surface 65c is a surface facing the inner peripheral surface 62b of the second nut member 62.

The dish portion 66 is formed at one end of the cylindrical portion 65. The dish portion 66 is a flange-shaped (eaves-shaped) portion extending outward from the outer peripheral surface 65c of the cylindrical portion 65. That is, an outer diameter of the dish portion 66 is larger than the outer diameter of the cylindrical portion 65. The outer diameter of the dish portion 66 is substantially the same as an outer diameter of the second nut member 62. The dish portion 66 is formed at the end portion of the first nut member 61 on the head portion 32 side (see FIG. 8).

In a plan view orthogonal to the central axis AX, the centers of the cylindrical portion 65, the dish portion 66, the hollow portion 62a, and the hollow portion 65a coincide with the central axis AX. The cylindrical portion 65, the dish portion 66, the hollow portion 62a, and the hollow portion 65a are circular in a plan view orthogonal to the central axis AX. The cylindrical portion 65, the dish portion 66, the hollow portion 62a, and the hollow portion 65a are concentric circles in a plan view orthogonal to the central axis AX.

As shown in FIG. 8, in the axial direction, the dish portion 66 is disposed between the second nut member 62 and the head portion 32. One surface of the dish portion 66 faces the head portion 32, and the other surface faces the second nut member 62. Then, as shown in FIGS. 8 and 9, a space S in which the first part 10 and the second part 20 are disposed is formed between the dish portion 66 and the head portion 32.

As shown in FIG. 6, the first nut member 61 includes a first pin 71. For example, the cylindrical portion 65 is formed with a pin hole 65h for fixing the first pin 71. The pin hole 65h is a through hole that reaches the inner peripheral surface 65b from the outer peripheral surface 65c of the cylindrical portion 65.

The first pin 71 is press-fitted into the pin hole 65h from the outer peripheral surface 65c side. The first pin 71 protrudes from the inner peripheral surface 65b toward the central axis AX side. The first pin 71 is disposed in the direction that passes through the central axis AX and that is extended along the direction orthogonal to the central axis AX. When the first pin 71 is inserted into the pin hole 65h, the first nut member 61 holds the first pin 71.

As shown in FIG. 9 the first pin 71 is inserted into the first spiral groove 41. Here, the first nut member 61 is provided with two first pins 71 and two pin holes 651x. The multiple first pins 71 are provided apart from each other in the circumferential direction. The two first pins 71 are disposed symmetrically with respect to the central axis AX. That is, the two first pins 71 are disposed on the same straight line orthogonal to the central axis AX. The two first pins 71 correspond to the two first spiral grooves 41. That is, one first pin 71 is inserted into one first spiral groove 41, and the other first pin 71 is inserted into the other first spiral groove 41.

In the axial direction, the first pin 71 is disposed between the dish portion 66 and the second pin 72. In the circumferential direction, the positions of the first pin 71 and the second pin 72 coincide with each other. The distance between the two first pins 71 in the circumferential direction is 180°, The distance between the two second pins 72 in the circumferential direction is 180°.

As shown in FIGS. 6 and 9, the cylindrical portion 65 is formed with an elongated hole 65d for inserting the second pin 72. The elongated hole 65d is a through hole that reaches the inner peripheral surface 65b from the outer peripheral surface 65c of the cylindrical portion 65. The elongated hole 65d extends through the cylindrical portion 65 along a direction orthogonal to the central axis AX. The cross-sectional shape of the elongated hole 65d is an elongated hole shape with the axial direction serving as the longitudinal direction.

Two elongated holes 65d are formed in the cylindrical portion 65. The two elongated holes 65d correspond to the two second pins 72. That is, one second pin 72 is inserted into one elongated hole 65d, and the other second pin 72 is inserted into the other elongated hole 65d. The size of the elongated hole 65d is larger than the diameter of the second pin 72. Thus, the second pin 72 is displaced along the longitudinal direction of the elongated hole 65d. That is, the second pin 72 moves in the axial direction in the elongated hole 65d. In the axial direction, the size of the elongated hole 65d in the longitudinal direction defines the amount of displacement (stroke) of the second pin 72 with respect to the first pin 71. That is, the axial distance between the first pin 71 and the second pin 72 changes by the size of the elongated hole 65d.

A spring 63 is provided between the second nut member 62 and the first nut member 61. For example, the second nut member 62 is provided with a recess portion or the like for disposing the spring 63. The spring 63 is, for example, a coil spring and is disposed along the axial direction. The spring 63 expands and contracts in the axial direction.

The spring 63 is disposed between the second nut member 62 and the dish portion 66. One end of the spring 63 is in contact with the second nut member 62 and the other end is in contact with the dish portion 66. The spring 63 urges the dish portion 66 in an urging direction shown by an arrow B in FIG. 8. That is, the spring 63 generates an urging force along the axial direction so as to separate the dish portion 66 from the second nut member 62.

Thus, as shown in FIG. 8, the spring 63 creates a gap G between the dish portion 66 and the second nut member 62. In this way, the spring 63 is disposed between the second nut member 62 and the first nut member 61. The spring 63 is an urging member that urges the first nut member 61 toward the head portion 32 of the bolt 30. In other words, the spring 63 urges the second nut member 62 in a direction away from the head portion 32. Of course, the urging member is not limited to the spring 63, and an elastic body such as resin may be used.

The spring 63 has, for example, an outer diameter of 3 mm and a natural length of 10 mm. The spring constant k=0.3 N/mm. The length of the spring at the time of mounting is 7 mm, and the mounting load is 0.9 N. The maximum expansion/contraction amount of the spring 63 is 5 mm, and the maximum load is 1.5 N. Since the spring 63 expands and contracts in the range of 5 mm to 7 mm, the size of the elongated hole 65d in the longitudinal direction is 2 mm.

A method of attaching the second nut member 62 and the first nut member 61 will be described. First, the first nut member 61 to which the first pin 71 is attached is prepared. Specifically, the first pin 71 is inserted into the pin hole 65h from the outer peripheral surface 65c side, By press-fitting the first pin 71 into the pin hole 65h, the first pin 71 is fixed to the first nut member 61. The first pin 71 protrudes from the inner peripheral surface 65b toward the central axis AX. Further, the second nut member 62 to which the second pin 72 is not attached is prepared.

The spring 63 is disposed between the first nut member 61 and the second nut member 62. Then, the cylindrical portion 65 is inserted into the hollow portion 62a of the second nut member 62. Here, the relative positions of the first nut member 61 and the second nut member 62 are adjusted so that the positions in the circumferential direction of the elongated hole 65d and the pin hole 62h match. As a result, the elongated hole 65d and the pin hole 62h are connected. The second pin 72 is inserted into the pin hole 65h and the elongated hole 65d from the outer peripheral surface 62c side. By press-fitting the second pin 72 into the pin hole 65h, the second pin 72 is fixed to the second nut member 62.

As a result, as shown in FIGS. 7 to 9, and the like, the second nut member 62 and the first nut member 61 are fixed. Since the second pin 72 protrudes from the inner peripheral surface 65b of the cylindrical portion 65 toward the central axis AX, the second nut member 62 and the first nut member 61 become unremovable.

As described above, the cylindrical portion 65 is provided with the elongated hole 65d extending in the axial direction. The second pin 72 is movable along the axial direction in the elongated hole 65d. The expansion and contraction of the spring 63 changes the distance between the first pin 71 and the second pin 72 in the axial direction. In other words, the elongated hole 65d defines the expansion and contraction length of the spring 63. The distance between the first pin 71 and the second pin 72 changes by the distance corresponding to the length of the elongated hole 65d in the axial direction.

Here, two springs 63 are disposed between the second nut member 62 and the first nut member 61. In the circumferential direction, the two springs 63 are disposed symmetrically with respect to the central axis AX. Specifically, the first pin 71, the spring 63, the first pin 71, and the spring 63 are disposed at intervals of 90° in the circumferential direction. Further, in the circumferential direction, the positions of the first pin 71 and the second pin 72 coincide with each other, Next, a method of attaching the bolt 30 and the nut 60 will be described with reference to FIGS. 7 to 9, and the like. The nut 60 is inserted into the shaft portion 31 of the bolt 30. That is, the shaft portion 31 is inserted into the hollow portion 65a. Here, the positions of the first pin 71 and the second pin 72 in the circumferential direction coincide with the slit 43, That is, the nut 60 is inserted into the bolt 30 so that the first pin 71 and the second pin 72 move along the slit 43. As it is inserted into the bolt 30, the first pin 71 and the second pin 72 move axially in the slit 43. Then, when the bolt 30 is inserted all the way, the first pin 71 reaches the first spiral groove 41. Here, when a force for contracting the spring 63 is applied to further push the member 62, the second pin 72 reaches the second spiral groove 42.

Next, the bolt 30 or nut 60 is rotated around the axis. That is, the bolt 30 rotates relative to the nut 60 about the axis. As a result, the first pin 71 moves along the first spiral groove 41, and the second pin 72 moves along the second spiral groove 42. That is, the first pin 71 spirally moves in the first spiral groove 41, and the second pin 72 spirally, moves in the second spiral groove 42. That is, as the boil 30 rotates, the first pin 71 moves from one end to the other end of the first spiral groove 41 in the axial direction and the circumferential direction. Similarly, the second pin 72 moves axially and circumferentially from one end to the other end of the second spiral groove 42. By rotating the bolt 30 or the nut 60 in the circumferential direction in this way, the bolt 30 and the nut 60 are screwed together.

When the second pin 72 moves to the other end of the second spiral groove 42, it reaches the loosening suppression groove 44. The spring 63 urges the second nut member 62 in a direction away from the dish portion 66. Thus, when the second pin 72 reaches the loosening suppression groove 44, it moves toward the tip end surface 34 side along the loosening suppression groove 44. That is, the second pin 72 is pushed back toward the tip end surface 34 side of the bolt 30. As a result, the second pin 72 moves to the end portion of the loosening suppression groove 44 on the tip end surface 34 side. Thus, the gap G between the dish portion 66 and the second nut member 62 becomes wider in the axial direction.

By doing so, the bolt 30 and the nut 60 are fixed. That is, the first part 10 and the second part 20 shown in FIG. 1 and the like are fastened in the space S between the head portion 32 of the bolt 30 and the dish portion 66 of the nut 60.

Since the spring 63 urges the second nut member 62 in the direction away from the head portion 32, the second pin 72 moves toward the tip end side in the loosening suppression groove 44. As a result, since the second pin 72 is restricted from moving along the second spiral groove 42, the bolt 30 and the nut 60 are suppressed from loosening. That is, it is possible to suppress the second pin 72 from returning from the other end of the second spiral groove 42 on the loosening suppression groove 44 side to one end on the slit 43 side. Thus, at the time of fastening, the relative rotation between the bolt 30 and the nut 60 is restricted, and the second pin 72 is not moved to the slit 43. Thus, it is possible to suppress the bolt 30 from coming off the nut 60 along the axial direction.

Next, a method of removing the bolt 30 and the nut 60 will be described. In the state where the bolt 30 and the nut 60 are fixed, the second pin 72 is inserted into the loosening suppression groove 44 as described above. That is, the second pin 72 is located on the tip end surface 34 side of the loosening suppression groove 44. The user pushes the second nut member 62 toward the head portion 32. That is, the user applies an axial force to the second nut member 62 so as to bring the second nut member 62 closer to the dish portion 66. Since the spring 63 contracts due to the force of the user, the second pin 72 moves toward the head portion 32 side along the loosening suppression groove 44. The user pushes in the second nut member 62 until the second pin 72 reaches the end portion of the loosening suppression groove 44 on the head portion 32 side. As a result, since the second pin 72 reaches the second spiral groove 42, the nut 60 can rotate around the axis.

Then, with the user pushing in the second nut member 62, the nut 60 is rotated around the axis. By doing so, the second pin 72 moves along the second spiral groove 42. When the second pin 72 moves from the other end to one end of the second spiral groove 42, the second pin 72 reaches the slit 43. Similarly, the first pin 71 moves along the first spiral groove 41. When the first pin 71 moves from the other end to one end of the first spiral groove 41, the first pin 71 reaches the slit 43.

This makes it possible to pull out the nut 60 from the bolt 30, That is, the nut 60 is moved in the axial direction so that the dish portion 66 of the nut 60 is separated from the head portion 32 of the bolt 30. The first pin 71 and the second pin 72 move toward the tip end surface 34 side along the slit 43. Thus, the user can remove the nut 60 from the bolt 30.

As described above, the peripheral surface 33 of the shaft portion 31 of the bolt 30 is provided with the first spiral groove 41, the second spiral groove 42, the slit 43, and the loosening suppression groove 44. Further, the nut 60 includes the first pin 71 that moves along the first spiral groove 41 and the second pin 72 that moves along the second spiral groove 42.

When the first pin 71 and the second pin 72 are located in the circumferential position of the slit 43, the user can move the nut 60 relative to the bolt 30 along the axial direction. The bolt 30 and the nut 60 can be fixed by just inserting the first pin 71 and the second pin 72 into the slit 43 and rotating the nut 60. Further, when the first pin 71 and the second pin 72 are located in the circumferential direction of the slit 43, the nut 60 can be removed from the bolt 30. When the first pin 71 and the second pin 72 deviate from the circumferential position of the slit 43, the nut 60 cannot be attached to or detached from the bolt 30.

Then, when the second pin 72 moves from one end to the other end of the second spiral groove 42, the spring 63 urges the second nut member 62 in the direction away from the head portion 32. Thus, the second pin 72 moves to the end portion on the tip end side of the loosening suppression groove 44. The movement and rotation of the nut 60 with respect to the bolt 30 is restricted. That is, the nut 60 cannot rotate about the axis and cannot move along the axial direction.

In other words, unless the user pushes the second nut member 62 toward the head portion 32 side, the nut 60 cannot be removed from the bolt 30. As a result, the bolt and the nut 60 can be securely fixed. Loosening of the nut 60 can be suppressed, and the two parts can be securely fastened. That is, it is possible to suppress the bolt 30 from coming off from the nut 60 when the parts are fastened.

Further, the bolt 30 and the nut 60 can be removed by just rotating the nut 60 around the shaft with the nut 60 pushed in. Thus, simple attachment and detachment is possible. No special tools are required for installation and removal. That is, attachment and detachment can be performed with the user's own hand or finger. Further, durability and workability can be improved.

Further, the nut 60 is provided with two first pins 71 and two second pins 72. Two first spiral grooves 41, two second spiral grooves 42, two slits 43, and two loosening suppression grooves 44 are formed on the peripheral surface 33 of the bolt 30. This makes it possible to more reliably suppress the nut 60 from loosening.

In this case, the formation range of one first spiral groove 41 may be set to less than 180° in the circumferential direction. As a result, the pair of first spiral grooves 41 can be formed symmetrically with respect to the central axis AX. Similarly, the formation range of one second spiral groove 42 may be set to less than 180°. As a result, the pair of second spiral grooves 42 can be formed symmetrically with respect to the central axis AX. Thus, it can be installed more reliably and easily.

The first spiral groove 41 may be formed thicker than the second spiral groove 42. For example, the groove width of the first spiral groove 41 can be about 1.5 mm, and the groove width of the second spiral groove 42 can be about 1.2 mm. The first pin 71 may be formed thicker than the second pin 72. The first pin 71 may be thicker than the second spiral groove 42 and thinner than the first spiral groove 41. By doing so, it is possible to suppress the first pin 71 from accidentally entering the second spiral groove 42. This makes it possible to suppress the first pin 71 from accidentally entering the second spiral groove 42 on the tip end side even when the user rotates the nut 60 in the middle of the stroke of the slit 43 in the axial direction. Thus, it is possible to suppress erroneous mounting.

Further, the parts may be fastened with a wave washer, an E ring, or the like sandwiched in the space S between the head portion 32 of the bolt 30 and the dish portion 66.

Figure 10:
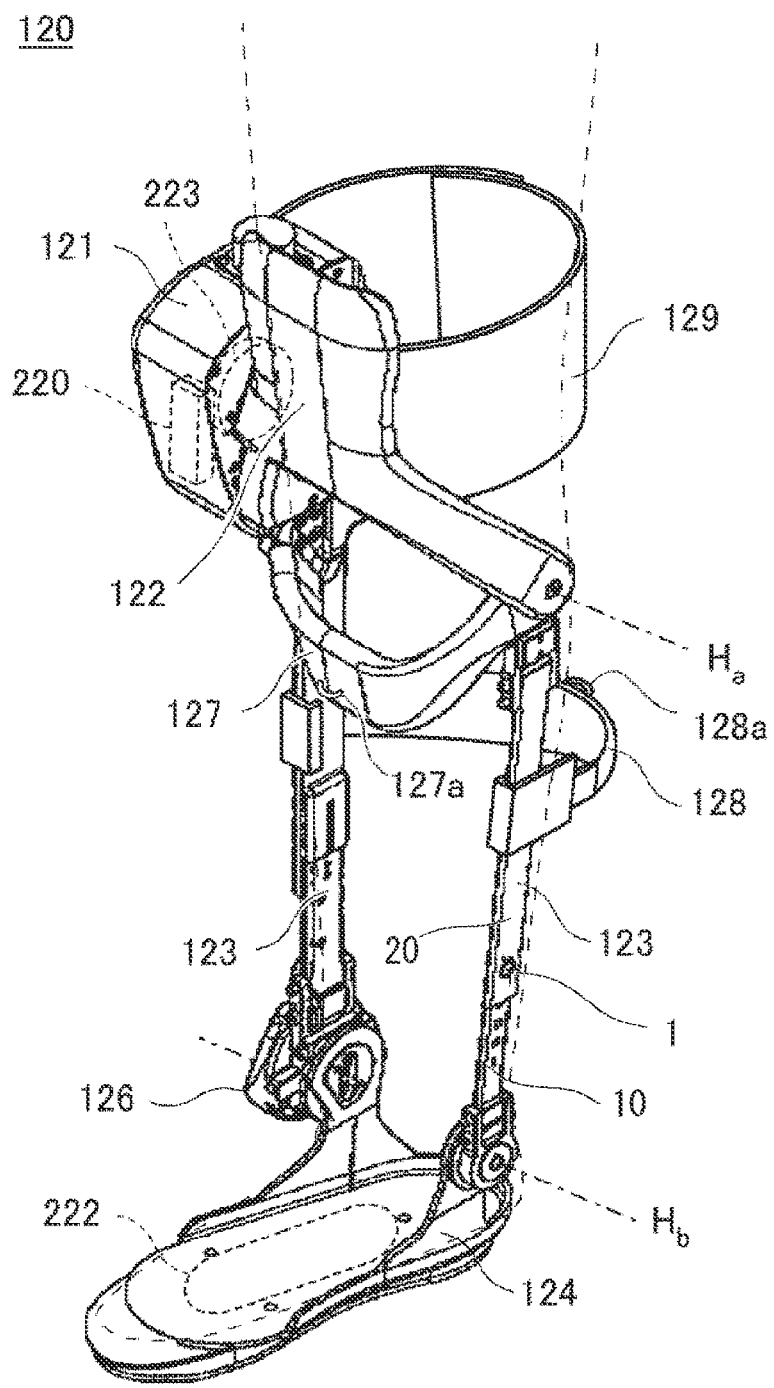
FIG. 10 is a schematic perspective view showing a mounting tool having the part fastening structure.

FIG. 10 is a diagram showing an example of a mounting tool using the part fastening structure 1. FIG. 10 is a perspective view schematically showing a mounting tool 120 worn by the user. The mounting tool 120 mainly includes a control unit 121, a plurality of frames that support each part of the affected leg, and a load sensor 222 for detecting a load applied to the sole of the foot. The mounting tool 120 functions as a walking assist device having a drive unit and a control unit.

The control unit 121 includes an auxiliary control unit 220 that controls the mounting tool 120, and also includes a motor (not shown) that generates a driving force for assisting the extension movement and the flexion movement of the knee joint. The frame supporting each part of the affected leg includes a thigh frame 122 and a lower leg frame 123 rotatably connected to the thigh frame 122. Further, this frame includes a foot flat frame 124 rotatably connected to the lower leg frame 123, a front side connecting frame 127, and a rear side connecting frame 128.

The thigh frame 122 and the lower leg frame 123 rotate relative to each other around a hinge axis $H_a$ shown in the figure. The motor of the control unit 121 rotates in accordance with an instruction of the auxiliary control unit 220 to assist the thigh frame 122 and the lower leg frame 123 to open or close relatively around the hinge axis $H_a$. An angle sensor 223 housed in the control unit 121 is, for example, a rotary encoder, and detects an angle formed by the thigh frame 122 and the lower leg frame 123 around the hinge axis $H_a$. The lower leg frame 123 and the foot flat frame 124 rotate relative to each other around the hinge axis $H_b$, shown in the figure. The relative rotating angle range is pre-adjusted by the adjusting mechanism 126.

The thigh frame 122 includes a thigh belt 129. The thigh belt 129 is a belt integrally provided on the thigh frame, and is wrapped around the thigh portion of the affected leg to fix the thigh frame 122 to the thigh portion. This suppresses the entire mounting tool 120 from shifting with respect to the trainee's legs.

The load sensor 222 is a load sensor embedded in the foot flat frame 124. The load sensor 222 can also be configured to detect the magnitude and distribution of the vertical load received by the trainee's sole, for example, to detect a center of pressure (COP), The load sensor 222 is, for example, a resistance change detection type load detection sheet in which electrodes are disposed in a matrix.

The lower leg frame 123 includes the first part 10 and the second part 20 shown in FIG. 1. Then, the first part 10 and the second part 20 are connected via the part fastening structure 1. That is, the user attaches the first part 10 and the second part 20 by the part fastening structure 1. Thus, the length of the lower leg frame 123 can be adjusted in accordance with the leg length of the user who wears the mounting tool 120. The user can easily and surely fasten the first part 10 and the second part 20 of the lower leg frame 123. Therefore, the user can easily adjust the frame length. The number of parts to be fastened by the part fastening structure 1 may be 3 or more.

Although the disclosure made by the present inventor has been specifically described above based on the embodiment, the present disclosure is not limited to the above embodiment and can be variously modified within a range that does not depart from the gist thereof.

What is claimed is:

1. A part fastening structure that fastens a part using a bolt and a nut,
   wherein the bolt includes:
   a first spiral groove provided on a peripheral surface of the bolt;
   a second spiral groove that is provided on the peripheral surface of the bolt and that is provided on a tip end side of the bolt with respect to the first spiral groove;
   a slit that is provided on the peripheral surface of the bolt along an axial direction, and that extends from a tip end of the bolt to the first spiral groove through the second spiral groove; and
   a loosening suppression groove that extends from another end of the second spiral groove to the tip end side,
   wherein the nut includes:
   a first nut member including a first pin that protrudes from an inner peripheral surface toward a central axis side and that is inserted into the first spiral groove;
   a second nut member including a second pin that protrudes from the inner peripheral surface toward the central axis side and that is inserted into the second spiral groove; and
   an urging member that is disposed between the first nut member and the second nut member and that urges the first nut member toward a head portion of the bolt.

2. The part fastening structure according to claim 1,
   wherein the first spiral groove is provided to be thicker than the second spiral groove,
   wherein the first pin is thicker than the second pin, and
   wherein the first pin is thicker than the second spiral groove.

3. The part fastening structure according to claim 1,
   wherein the first nut member includes:
   a cylindrical portion; and
   a dish portion protruding from the cylindrical portion to an outer peripheral side,
   wherein the second nut member is disposed on the outer peripheral side of the cylindrical portion,
   wherein the cylindrical portion is provided with a through hole extending through the cylindrical portion in a direction orthogonal to the axial direction,
   wherein the through hole is an elongated hole in which a longitudinal direction coincides with the axial direction, and
   wherein the second pin extends through the through hole.

4. The part fastening structure according to claim 3,
   wherein the urging member is disposed between the dish portion and the second nut member.

5. The part fastening structure according to claim 1,
   wherein the first nut member is provided with a plurality of the first pins spaced away from each other in a circumferential direction,
   wherein the second nut member is provided with a plurality of the second pins spaced away from each other in the circumferential direction,
   wherein a plurality of the first spiral grooves is provided corresponding to the first pins,
   wherein a plurality of the second spiral grooves is provided corresponding to the second pins, and
   wherein a circumferential angle of the first spiral grooves and the second spiral grooves is less than 180°.

6. The part fastening structure according to claim 1,
   wherein the nut is provided with two first pins and two second pins,
   wherein the two second pins are disposed so as to face each other with a central axis in between, and
   wherein the too first pins are disposed so as to face each other with the central axis in between.

7. A mounting tool that is worn by a user, the mounting tool comprising:
   a first part including a plurality of first through holes;
   a second part including a second through hole; and
   the part fastening structure according to claim 1,
   wherein the bolt is inserted through the first through hole and the second through hole.

* * * * *